(12) United States Patent
Kuo

(10) Patent No.: US 6,406,478 B1
(45) Date of Patent: Jun. 18, 2002

(54) BONE REINFORCEMENT PLATE FOR USE ON THE SPINE

(76) Inventor: Robert W. H. Kuo, 3rd Fl., No. 1, Lane 43, Sec. 1, Chang-An E. Rd., Taipei (TW)

( * ) Notice: Subject to any disclaimer, the term of this patent is extended or adjusted under 35 U.S.C. 154(b) by 0 days.

(21) Appl. No.: 09/863,429

(22) Filed: May 24, 2001

(51) Int. Cl.[7] .............................................. A61B 17/80
(52) U.S. Cl. ........................................ 606/71; 606/69
(58) Field of Search ............................... 606/69, 70, 71

(56) References Cited

U.S. PATENT DOCUMENTS

| | | | | |
|---|---|---|---|---|
| 4,794,918 A | * | 1/1989 | Wolter | 606/69 |
| 5,290,288 A | * | 3/1994 | Vignaud et al. | 606/69 |
| 5,324,290 A | * | 6/1994 | Zdeblick et al. | 606/69 |
| 5,344,421 A | * | 9/1994 | Crook | 606/71 |
| 5,527,311 A | * | 6/1996 | Procter et al. | 606/69 |
| 5,549,612 A | * | 8/1996 | Yapp et al. | 606/69 |
| 5,665,089 A | * | 9/1997 | Dall et al. | 606/70 |
| 5,681,311 A | * | 10/1997 | Foley et al. | 606/69 |
| 6,206,882 B1 | * | 3/2001 | Cohen | 606/69 |

* cited by examiner

*Primary Examiner*—Paul J. Hirsch
(74) *Attorney, Agent, or Firm*—Rosenberg, Klein & Lee

(57) ABSTRACT

A bone reinforcement plate for the spine has a cover and a base detachably engaged with the cover and having through holes and slots. Each slot has a wavy inner periphery. Fasteners are selectively inserted into the through holes and slots and abutted by the cover.

4 Claims, 6 Drawing Sheets

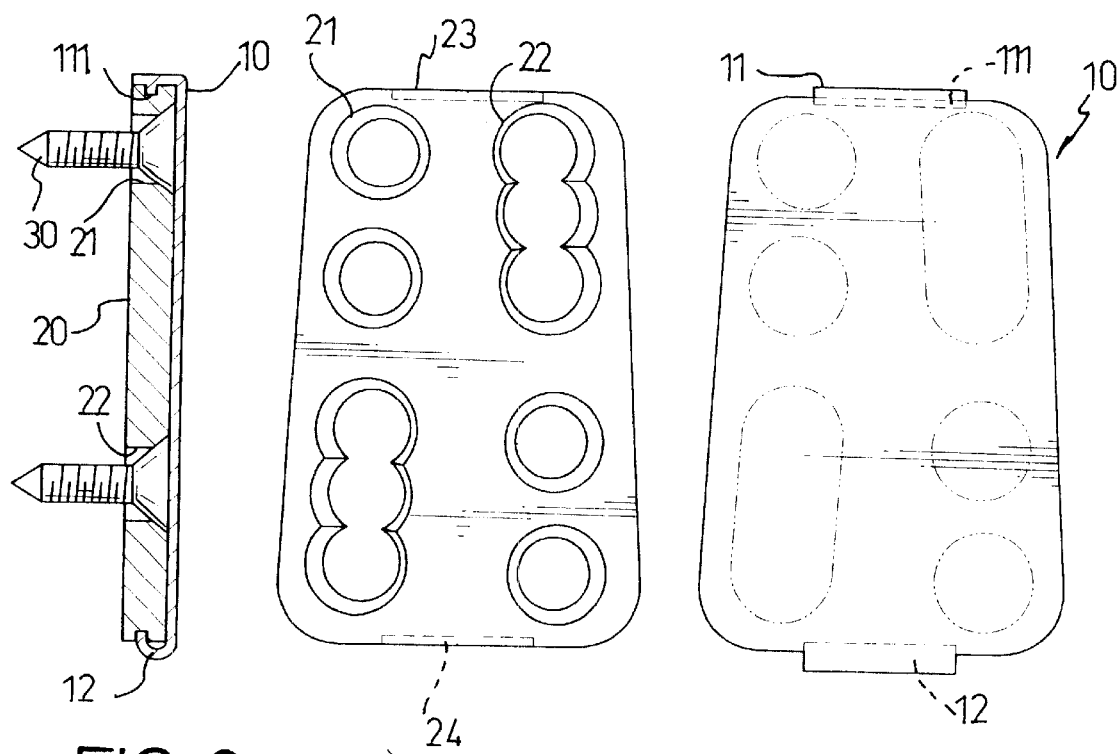
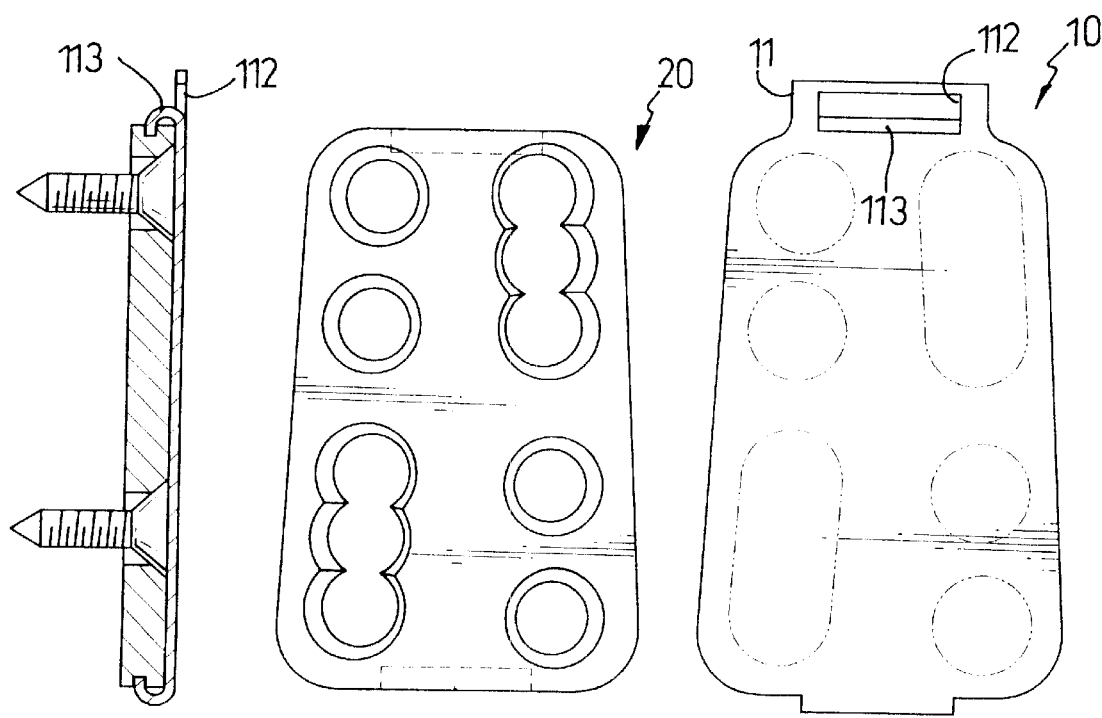

BONE REINFORCEMENT PLATE FOR USE ON THE SPINE

BACKGROUND OF THE INVENTION

1. Field of the Invention

The present invention relates to a bone reinforcement plate, and more particularly to a bone reinforcement plate especially applicable to the spine.

2. Description of Related Art

With reference to FIG. 7, a conventional bone reinforcement plate (50) is used to reinforce the bone to hold bone fragments in place and prevent further cracking of the bone. The bone reinforcement plate (50) has multiple through holes (51) and slots (52) defined through the bone reinforcement plate (50). On the bone reinforcement plate (50), the holes (51) and slots (52) are in pairs composed of holes-slot combination (A), slot-slot combination (B) and holes-holes combination (C).

With reference to FIGS. 8 and 9, when the bone reinforcement plate (50) is used, bone screws (53) with tapered heads (531) are inserted through the through holes (51) and slots (52) and screwed into the spine (40) until the end of the tapered head (531) is flush with bone reinforcement plate (50). The bone screws (53) are selectively inserted through both sides of the bone reinforcement plate (50). Auxiliary locking screws (54) have thin, flat heads (541). An auxiliary locking screw (54) is screwed into the bone reinforcement plate (50) next to each of the bone screws (53). The thin, flat head (541) of the auxiliary locking screw (54) overlaps the head (531) of the bone screw (53) to lock the bone screw (53) to the bone reinforcement plate (50). Thereafter, an area covered by the bone reinforcement plate (50) is held in place and protected from further cracking.

When the conventional bone reinforcement plate (50) is used, too many retainers (screws) are required not only to secure the spine structure, but also to secure the bone reinforcement plate (50) onto the spine (40), which causes an additional burden to the patient bearing the bone reinforcement plate (50). Furthermore, as time goes by, the fasteners (screws) will gradually surface themselves due to the movement of the spine. If that situation happens, the patient still requires another operation to reposition the fasteners to regain the required effect on the spine. In conclusion, implanting and maintaining the bone reinforcement plate (50) in position is costly and troublesome.

To overcome the shortcomings, the present invention tends to provide an improved bone reinforcement plate to mitigate and obviate the aforementioned problems.

SUMMARY OF THE INVENTION

The primary objective of the present invention is to have a bone reinforcement plate having a cover detachably yet securely engaged with a base with multiple through holes and slots so that no additional fasteners are required.

Another objective of the invention is to provide a bone reinforcement plate, wherein each of the slots is composed of holes communicating with each other.

Still another objective of the invention is to have a bolt and nut combination to further enhance the connection between the cover and the base.

Other objects, advantages and novel features of the invention will become more apparent from the following detailed description when taken in conjunction with the accompanying drawings.

BRIEF DESCRIPTION OF THE DRAWINGS

FIG. 2 is a side plan view of the bone reinforcement plate in FIG. 1;

FIG. 3 is a cross sectional view of the assembled cover and base of the bone reinforcement plate of FIG. 1;

FIG. 5 is a side plan view of the bone reinforcement plate of FIG. 4;

FIG. 6 is a cross sectional view of a still another preferred embodiment of the present invention;

DETAILED DESCRIPTION OF PREFERRED EMBODIMENT

Figure 1:
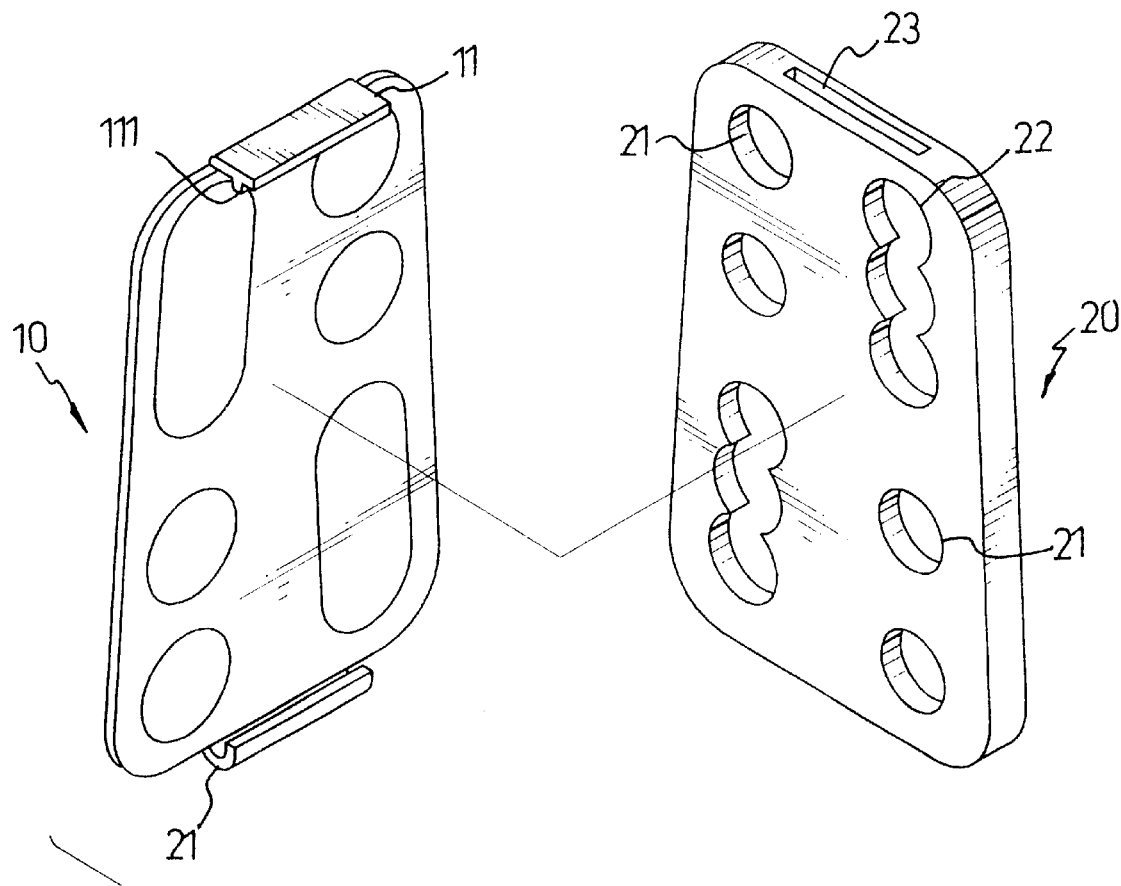
FIG. 1 is an exploded perspective view of the bone reinforcement plate in accordance with the present invention.

With reference to FIGS. 1 and 2, a bone reinforcement plate (1) in accordance with the present invention has a cover (10) and a base (20).

The cover (10) is detachably connected to the base (20) and has a wing (11) extending perpendicularly to an upper edge of the cover (10). A rib (111) is integrally formed on the wing (111). The cover (1) further has a lower resilient hook (12) formed to oppose the wing (11) and rib (111).

The base (20) has multiple through holes (21), slots (22), an upper recess (23) and a lower recess (24). The upper recess (23) is defined to correspond to the rib (111) on the wing (11) and the lower recess (24) is defined to correspond to the lower resilient hook (12) on the cover (10). Each of the slots (22) is composed of overlapping holes, such that the slot has a wavy inner periphery.

With reference to FIG. 3, when the cover (10) and the base (20) are used, suitable fasteners such as bone screws (30) are inserted into suitable holes (21) and/or slots (22) and screwed into the bone tissue to hold the spine in position. Thereafter, the rib (111) on the cover (10) is first inserted into the corresponding upper recess (23). Then the lower resilient hook (12) is inserted into the corresponding lower recess (24) in the base (20). Due to the resilience of the hook (12), the cover (10) is able to be firmly engaged with the base (20) to securely abut the screws (30) to maintain the screws (30) rigidly in position. Furthermore, because of the wavy inner periphery of the slots (22), when the screws (30) are inserted into the slots (22), the screws (30) are securely held in one position in the slot (22) so that the bone screw (30) will not slip in the slot, which helps to secure the relative position of the base (20) to the spine.

Figure 4:
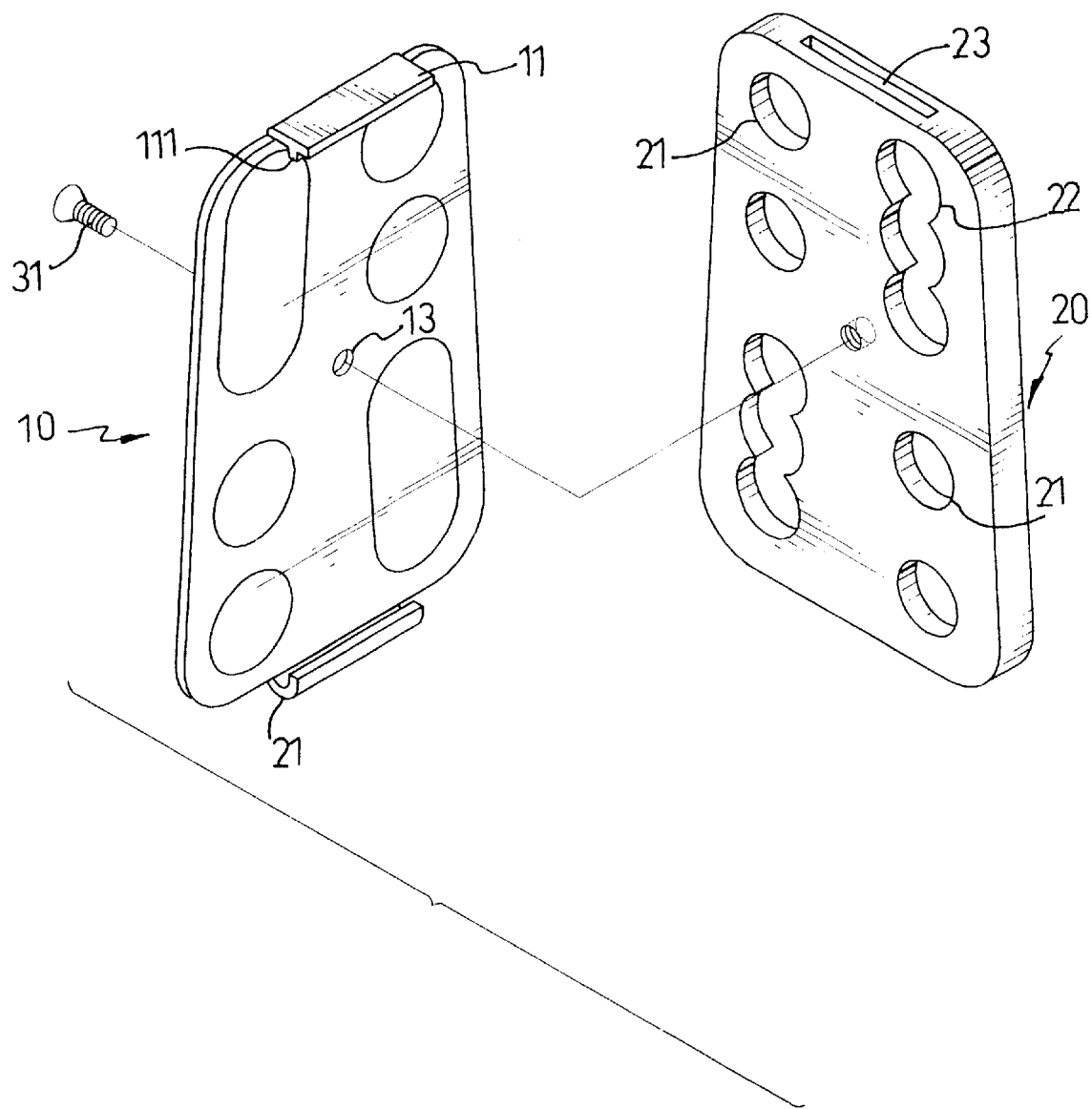
FIG. 4 is an exploded perspective view of another preferred embodiment of the bone reinforcement plate in accordance with the present invention.
Figure 7:
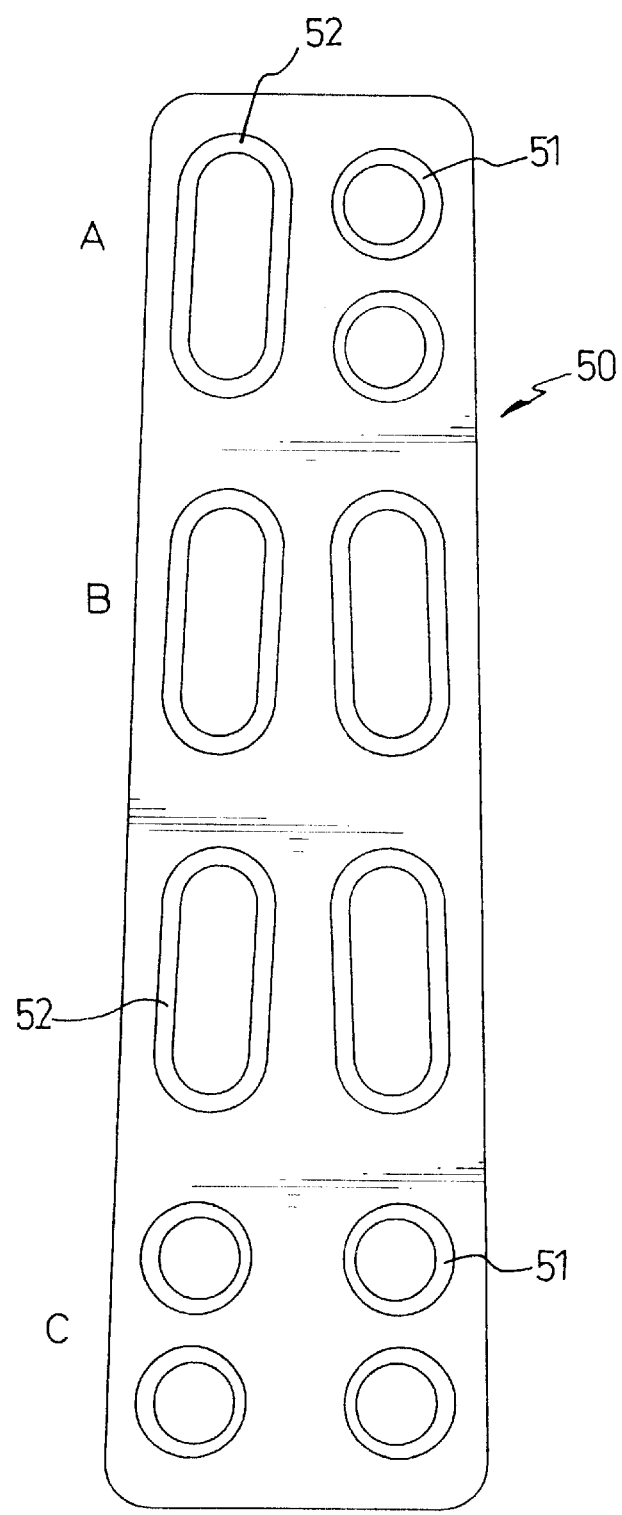
FIG. 7 is a side plan view of a conventional bone reinforcement plate.
Figure 8:
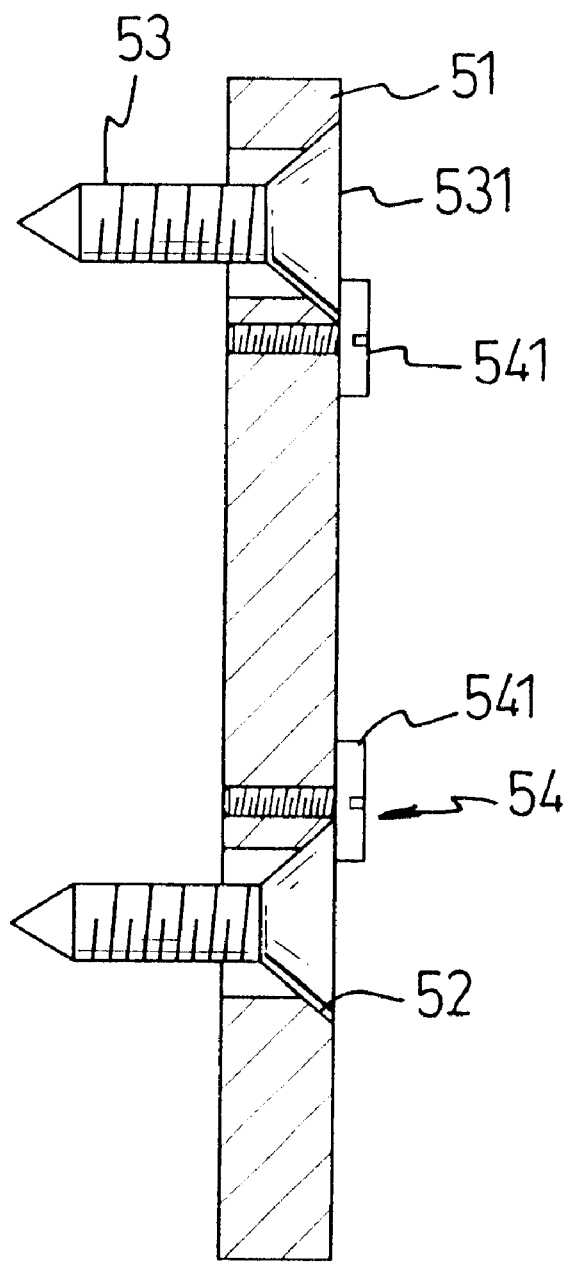
FIG. 8 is a cross sectional view of the conventional bone reinforcement plate of FIG. 7, wherein screws are inserted through the holes and slots.
Figure 9:
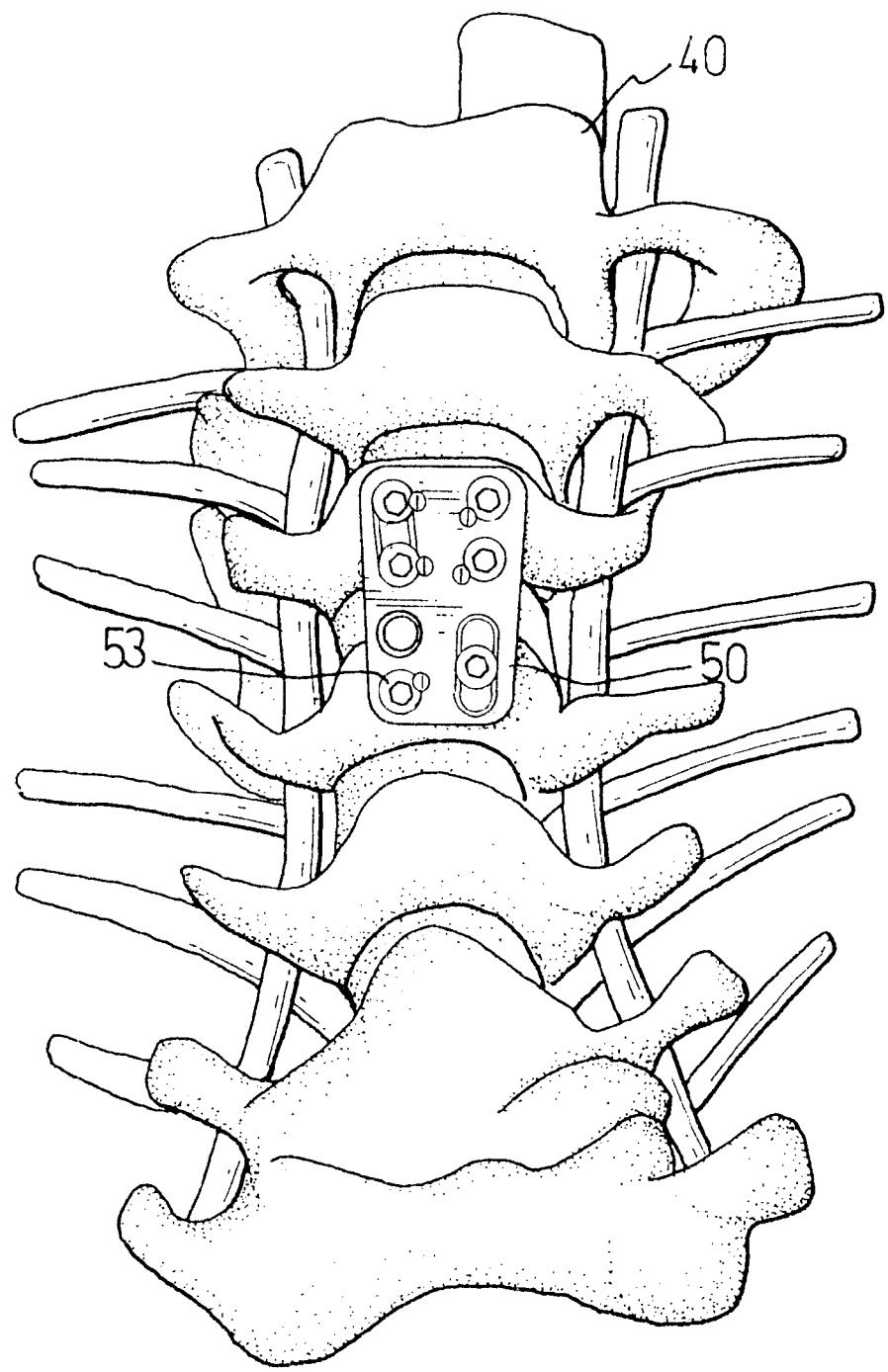
FIG. 9 is a top plan view of the bone reinforcement plate that is applied to spine.

With reference to FIG. 4, to further secure the cover (10) to the base (20), the base (20) has a first bore (25) and the cover (20) has a second bore (13) aligning with the first bore (25). Accordingly, after the base (20) is secured to the spine, and the cover (10) is attached to the base (20) with the rib (111) and hook (12), a suitable fastener such as a bolt (31) is screwed into the aligned first and second bores (25,13) to further secure the screws (30) in the predetermined positions.

With reference to FIGS. 5 and 6, another preferred embodiment of the present invention shows that the cover (10) has a wing (11) with an opening (112) and a second hook (113) formed along the peripheral edge of the opening (112) and oppositely symmetrical with respect to the resilient hook (12).

It is concluded that the bone reinforcement plate in accordance with the present invention is advantageous in that:

Light weight: since no extra screws are required to secure the screws in the slots or the holes, the overall weight of the plate of the present invention is much lighter than the conventional one.

Secured mutual engagement: by either the rib-hook combination of the cover in association with the upper and lower recesses of the base or the hook-hook combination of the cover in association with the upper and lower recesses of the base, the mutual engagement between the cover and the base is secured and thus the screws within the base are also secured.

Enhanced engagement: a first and a second bore are respectively defined in the base and the cover to allow a bolt to further secure the mutual engagement between the cover and the base, such that not only the mutual engagement between the cover and the base is secured, but also the positions of the screws within the base are also enhanced.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A bone reinforcement plate for use on a spine, the bone reinforcement plate comprising:

a cover, the cover having a wing extending perpendicularly from an upper edge of the cover and provided with a rib integrally formed with the wing and a lower resilient hook;

a base detachably engaged with the cover and having through holes and slots each with a wavy inner periphery formed by overlapping holes, the base having an upper recess formed therein to correspond to the rib and a lower recess formed therein to correspond to the lower resilient hook; and fasteners selectively inserted into the through holes and slots to secure the base to a spine, the fasteners being abutted by the cover to secure the fasteners in position, whereby engagement between the cover and the base is secured by the rib being received in the upper recess and the lower resilient hook is received in the lower recess.

2. The bone reinforcement plate as claimed in claim 1, wherein the base further has a first bore and the cover has a second bore aligned with the first bore for engagement by a bolt passed through the second bore and threadedly secured to the first bore to further secure the engagement between the cover and the base.

3. A bone reinforcement plate for use on a spine, the bone reinforcement plate comprising:

a cover, the cover having a wing extending perpendicularly from an upper edge of the cover and provided with an opening and an upper hook formed along a peripheral edge of the opening, the cover having a lower resilient hook formed symmetrically with respect to the upper hook at a lower end of the cover;

a base detachably engaged with the cover and having through holes and slots each with a wavy inner periphery formed by overlapping holes, the base having an upper recess formed therein to receive the upper hook therein and a lower recess formed in the base to receive the lower resilient hook therein for securement of the cover to the base; and fasteners selectively inserted into the through holes and slots to secure the base to a spine, the fasteners being abutted by the cover to secure the fasteners in position.

4. The bone reinforcement plate as claimed in claim 3, wherein the base further has a first bore and the cover has a second bore aligned with the first bore for engagement by a bolt passed through the second bore and threadedly secured to the first bore to further secure the engagement between the cover and the base.

* * * * *